United States Patent
Dai et al.

(10) Patent No.: US 8,663,207 B2
(45) Date of Patent: *Mar. 4, 2014

(54) SYSTEMS AND METHODS FOR EVALUATING TREATMENT TABLES FOR REFRACTIVE SURGERY

(71) Applicant: AMO Development, LLC, Santa Ana, CA (US)

(72) Inventors: Guang-ming Dai, Fremont, CA (US); Richard A. Hofer, Santa Cruz, CA (US); Dimitri Chernyak, Sunnyvale, CA (US)

(73) Assignee: AMO Development, LLC, Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/854,760

(22) Filed: Apr. 1, 2013

(65) Prior Publication Data

US 2013/0282350 A1    Oct. 24, 2013

Related U.S. Application Data

(63) Continuation of application No. 12/749,751, filed on Mar. 30, 2010, now Pat. No. 8,409,178.

(51) Int. Cl.
*A61F 9/008* (2006.01)
*A61B 3/00* (2006.01)
*A61B 3/10* (2006.01)
*A61B 5/05* (2006.01)

(52) U.S. Cl.
USPC ............... 606/4; 351/205; 351/246; 600/356

(58) Field of Classification Search
USPC .............. 606/4–5, 10–12; 351/200, 205–206, 351/210, 221–222, 246; 600/356
See application file for complete search history.

(56) References Cited

U.S. PATENT DOCUMENTS

| | | | |
|---|---|---|---|
| 4,665,913 A | 5/1987 | L'Esperance, Jr. |
| 4,669,466 A | 6/1987 | L'Esperance |
| 4,732,148 A | 3/1988 | L'Esperance, Jr. |
| 4,770,172 A | 9/1988 | L'Esperance, Jr. |
| 4,773,414 A | 9/1988 | L'Esperance, Jr. |
| 5,108,388 A | 4/1992 | Trokel |
| 5,163,934 A | 11/1992 | Munnerlyn |
| 5,207,668 A | 5/1993 | L'Esperance, Jr. |
| 5,219,343 A | 6/1993 | L'Esperance, Jr. |
| 5,646,791 A | 7/1997 | Glockler |
| 5,683,379 A | 11/1997 | Hohla |
| 5,713,892 A | 2/1998 | Shimmick |

(Continued)

FOREIGN PATENT DOCUMENTS

| | | |
|---|---|---|
| DE | 102005006897 A1 | 8/2006 |
| WO | 02/07660 A | 1/2002 |
| WO | 2010/049157 A1 | 5/2010 |

OTHER PUBLICATIONS

International Search Report and Written Opinion for PCT/US2011/030570 mailed on Aug. 10, 2011, 11 pages.

*Primary Examiner* — Dawayne A Pinkney
(74) *Attorney, Agent, or Firm* — AMO Development, LLC

(57) ABSTRACT

Treatment table verification techniques involve comparing intended refraction information with expected optical refraction information, and validating or qualifying the treatment table based on such comparisons. Systems and methods for verifying treatment tables provide enhanced safety for laser vision correction treatments.

20 Claims, 9 Drawing Sheets

(56) References Cited

U.S. PATENT DOCUMENTS

| | | |
|---|---|---|
| 5,807,379 A | 9/1998 | L'Esperance, Jr. |
| 6,004,313 A | 12/1999 | Shimmick et al. |
| 6,095,651 A | 8/2000 | Williams et al. |
| 6,203,539 B1 | 3/2001 | Shimmick et al. |
| 6,245,059 B1 | 6/2001 | Clapham |
| 6,271,915 B1 | 8/2001 | Frey et al. |
| 6,315,413 B1 | 11/2001 | Shimmick et al. |
| 6,331,177 B1 | 12/2001 | Munnerlyn et al. |
| 6,428,533 B1 | 8/2002 | Bille |
| 6,547,393 B2 | 4/2003 | Ruiz |
| 6,887,232 B2 | 5/2005 | Bille |
| 7,232,436 B2 | 6/2007 | Bille |
| 7,273,277 B2 | 9/2007 | Sarver |
| 7,296,893 B2 | 11/2007 | Dai |
| 7,460,288 B2 | 12/2008 | Liang |
| 7,926,490 B2 | 4/2011 | Dai et al. |
| 8,409,178 B2 | 4/2013 | Dai et al. |
| 2003/0053030 A1 | 3/2003 | Levine |
| 2005/0096640 A1 | 5/2005 | Dai et al. |
| 2006/0173445 A1 | 8/2006 | Bille |
| 2007/0222948 A1* | 9/2007 | Dai ................. 351/212 |
| 2008/0033408 A1 | 2/2008 | Bueler et al. |
| 2008/0058778 A1 | 3/2008 | Liedel et al. |
| 2010/0114076 A1* | 5/2010 | Reinstein et al. ........... 606/4 |
| 2013/0100410 A1* | 4/2013 | Liang ................. 351/223 |

* cited by examiner

SYSTEMS AND METHODS FOR EVALUATING TREATMENT TABLES FOR REFRACTIVE SURGERY

CROSS-REFERENCES TO RELATED APPLICATIONS

This application is a continuation of U.S. patent application Ser. No. 12/749,751 filed Mar. 30, 2010, which is related to U.S. patent application Ser. No. 10/825,864 filed Dec. 20, 2004, the entire content of which is incorporated herein by reference for all purposes.

BACKGROUND OF THE INVENTION

Embodiments of the present invention relate generally to the field of optical correction, and in particular encompass methods, devices, and systems for evaluating treatment tables for use in treating patients presenting vision conditions.

In a typical refractive surgical procedure, aberrations of the patient's eye are examined with wavefront analysis or other measurement procedures. In turn, the measurement information can be used to generate a treatment table for the patient. Laser eye surgery systems and other vision treatment techniques often involve the use of such treatment tables.

A laser treatment table can include, for example, a listing of coordinate references for delivery of a laser beam during an ablation of the cornea. In some cases, a treatment table includes the value of the discrete radial and angular positions of the optomechanical elements used to scan an image over a portion of the anterior corneal surface. Treatment tables may also contain laser pulse instructions such as size, location, sequence, and the number of laser pulses per position. In order to provide a patient with an effective, predictable, and safe surgical procedure, it is important to generate and implement a treatment table which is accurate.

Although current and proposed treatment devices and methods may provide real benefits to patients in need thereof, still further advances would be desirable. For example, there continues to be a need for improved ablation systems and methods that accurately assess, verify, and validate treatment tables. Embodiments of the present invention provide solutions that address certain limitations which may be associated with known techniques, and hence provide answers to at least some of these outstanding needs.

BRIEF SUMMARY OF THE INVENTION

Embodiments of the present invention encompass systems and methods for validating or qualifying treatment tables for use in refractive surgery procedures. These techniques ensure that treatment tables are generated as intended for a particular patient, and are not created unexpectedly. Exemplary validation techniques involve the use of a standalone, independent procedure which includes comparing an intended refraction with an expected optical refraction based on a treatment table that is intended for use with the patient. In some cases, the treatment table is qualified or approved to be released for use only if the difference between the intended refraction and the expected refraction is within a pre-defined tolerance. Hence, embodiments of the present invention provide improvements in ablation control, laser, ablation profile generation, treatment generation, and process or software verification and validation. Relatedly, techniques for evaluating a treatment table as described herein can be used to increase the safety of an ophthalmologic refractive surgery.

In an exemplary approach, laser pulse instructions, which may include size, location, and sequence information, can be used to derive an expected optical refraction, which is then compared with an intended refraction for the patient. Some evaluation or verification methods may include inputting a treatment table containing laser ablation instructions, and calculating an expected optical refraction based on the laser instructions, where the expected refraction includes sphere, cylinder, and axis components. Methods may also include inputting an intended optical refraction for a patient, where the intended refraction includes sphere, cylinder, and axis components, and evaluating or verifying the treatment table by comparing the expected and intended refractions. If the expected refraction is sufficiently similar to the intended refraction, the treatment table may be approved for use. If the expected refraction deviates significantly from the intended refraction, however, the treatment table can be disqualified. Hence, embodiments of the present invention provide a beneficial safety feature for refractive surgery procedures.

In a first aspect, embodiments of the present invention encompass methods of evaluating a treatment table for use in an ophthalmologic refractive surgery for a patient. Methods may include, for example, inputting a treatment table containing laser ablation instructions for treating the patient into a treatment instructions module, determining a simulated ablation for the patient based on the laser ablation instructions with a simulation ablation module, inputting a pupil dimension of the patient into a pupil dimension module, and determining an expected optical refraction for the patient based on the pupil dimension and the simulated ablation with an expected optical refraction module, where the expected optical refraction for the patient is dependent on a sphere ophthalmic term characterized by a set of second radial order polynomial terms, a cylinder ophthalmic term characterized by the set of second radial order polynomial terms, and an axis ophthalmic term characterized by the set of second radial order polynomial terms, and where the expected optical refraction profile is independent of a piston ophthalmic term characterized by a zero radial order polynomial term, an x-tilt ophthalmic term characterized by a set of first radial order polynomial terms, and a y-tilt ophthalmic term characterized by the set of first radial order polynomial terms. Methods may further include inputting an intended optical refraction for the patient into an intended refraction module, where the intended optical refraction for the patient is dependent on a sphere ophthalmic term, a cylinder ophthalmic term, and an axis ophthalmic term, and where the intended optical refraction profile is independent of a piston ophthalmic term, an x-tilt ophthalmic term, and a y-tilt ophthalmic term. Additionally, methods may include evaluating the treatment table by comparing the expected and intended optical refractions for the patient with a comparison module. In some cases, the set of second radial order polynomial terms includes a set of second radial order Zernike polynomial terms, the zero radial order polynomial term includes a zero radial order Zernike polynomial term, and the set of first radial order polynomial terms includes a set of first radial order Zernike polynomial terms. In some cases, the set of second radial order polynomial terms includes a set of second radial order Seidel power series terms, the zero radial order polynomial term includes a zero radial order Seidel power series term, and the set of first radial order polynomial terms includes a set of first radial order Seidel power series terms. Optionally, the expected optical refraction and the intended optical refraction each correspond to a common plane. In some instances, the expected optical refraction and the intended optical refraction each correspond to a corneal plane. In some instances, the pupil dimension of the patient corresponds to a wavefront diameter related to a wavescan of the patient. In some instances, the pupil dimensional of the patient comprises a pupil diameter that is equivalent to the wavefront diameter. According to some embodiments, the pupil dimension of the patient is a pupil diameter of about 4 mm. Methods may also include determining if a difference between the expected and intended optical refractions for the patient is within a pre-defined tolerance. Methods may also include qualifying the treatment table for use in the ophthalmologic refractive surgery for the patient if the difference between the expected and intended optical refractions is within the pre-defined tolerance. Some method may include disqualifying the treatment table for use in the ophthalmologic refractive surgery for the patient if the difference between the expected and intended optical refractions is not within the pre-defined tolerance.

In another aspect, embodiments of the present invention encompass systems for evaluating a treatment table for use in an ophthalmologic refractive surgery for a patient. Exemplary systems may include a treatment instructions module that accepts a treatment table containing laser ablation instructions for treating the patient, a simulation ablation module having a tangible medium embodying machine-readable code that determines a simulated ablation for the patient based on the laser ablation instructions, a pupil dimension module that accepts a pupil dimension of the patient, and an expected optical refraction module having a tangible medium embodying machine-readable code that determines an expected optical refraction for the patient based on the pupil dimension and the simulated ablation, where the expected optical refraction for the patient is dependent on a sphere ophthalmic term characterized by a set of second radial order polynomial terms, a cylinder ophthalmic term characterized by the set of second radial order polynomial terms, and an axis ophthalmic term characterized by the set of second radial order polynomial terms, and where the expected optical refraction profile is independent of a piston ophthalmic term characterized by a zero radial order polynomial term, an x-tilt ophthalmic term characterized by a set of first radial order polynomial terms, and a y-tilt ophthalmic term characterized by the set of first radial order polynomial terms. Systems may further include an intended refraction module that accepts an intended optical refraction for the patient, where the intended optical refraction for the patient is dependent on a sphere ophthalmic term, a cylinder ophthalmic term, and an axis ophthalmic term, and where the intended optical refraction profile is independent of a piston ophthalmic term, an x-tilt ophthalmic term, and a y-tilt ophthalmic term. Additionally, systems may include a comparison module having a tangible medium embodying machine-readable code that evaluates the treatment table by comparing the expected and intended optical refractions for the patient. In some system embodiments, the set of second radial order polynomial terms includes a set of second radial order Zernike polynomial terms, the zero radial order polynomial term includes a zero radial order Zernike polynomial term, and the set of first radial order polynomial terms includes a set of first radial order Zernike polynomial terms. In some systems, the expected optical refraction and the intended optical refraction each correspond to a common plane. In some systems, the expected optical refraction and the intended optical refraction each correspond to a corneal plane. Exemplary systems may also include a validation module having a tangible medium embodying machine-readable code that determines if a difference between the expected and intended optical refractions for the patient is within a pre-defined tolerance, and a qualification module having a tangible medium embodying machine-readable code that qualifies the treatment table for use in the ophthalmologic refractive surgery for the patient if the difference between the expected and intended optical refractions is within the pre-defined tolerance.

In another aspect, embodiments of the present invention encompass a computer program product embodied on a tangible computer readable medium that includes computer code for inputting a treatment table containing laser ablation instructions for treating the patient, computer code for determining a simulated ablation for the patient based on the laser ablation instructions, computer code for inputting a pupil dimension of the patient, and computer code for determining an expected optical refraction for the patient based on the pupil dimension and the simulated ablation, where the expected optical refraction for the patient is dependent on a sphere ophthalmic term characterized by a set of second radial order polynomial terms, a cylinder ophthalmic term characterized by the set of second radial order polynomial terms, and an axis ophthalmic term characterized by the set of second radial order polynomial terms, and where the expected optical refraction profile is independent of a piston ophthalmic term characterized by a zero radial order polynomial term, an x-tilt ophthalmic term characterized by a set of first radial order polynomial terms, and a y-tilt ophthalmic term characterized by the set of first radial order polynomial terms. Computer program products may also include computer code for inputting an intended optical refraction for the patient, where the intended optical refraction for the patient is dependent on a sphere ophthalmic term, a cylinder ophthalmic term, and an axis ophthalmic term, and where the intended optical refraction profile is independent of a piston ophthalmic term, an x-tilt ophthalmic term, and a y-tilt ophthalmic term, and computer code for evaluating the treatment table by comparing the expected and intended optical refractions for the patient with a comparison module. For some computer program products, the set of second radial order polynomial terms includes a set of second radial order Zernike polynomial terms, the zero radial order polynomial term includes a zero radial order Zernike polynomial term, and the set of first radial order polynomial terms includes a set of first radial order Zernike polynomial terms. For some computer program products, the expected optical refraction and the intended optical refraction each correspond to a common plane. For some computer program products, the expected optical refraction and the intended optical refraction each correspond to a corneal plane. Exemplary computer program products may also include computer code for determining if a difference between the expected and intended optical refractions for the patient is within a pre-defined tolerance, and computer code for qualifying the treatment table for use in the ophthalmologic refractive surgery for the patient if the difference between the expected and intended optical refractions is within the pre-defined tolerance.

For a fuller understanding of the nature and advantages of the present invention, reference should be had to the ensuing detailed description taken in conjunction with the accompanying drawings.

DETAILED DESCRIPTION OF THE INVENTION

Figure 1:
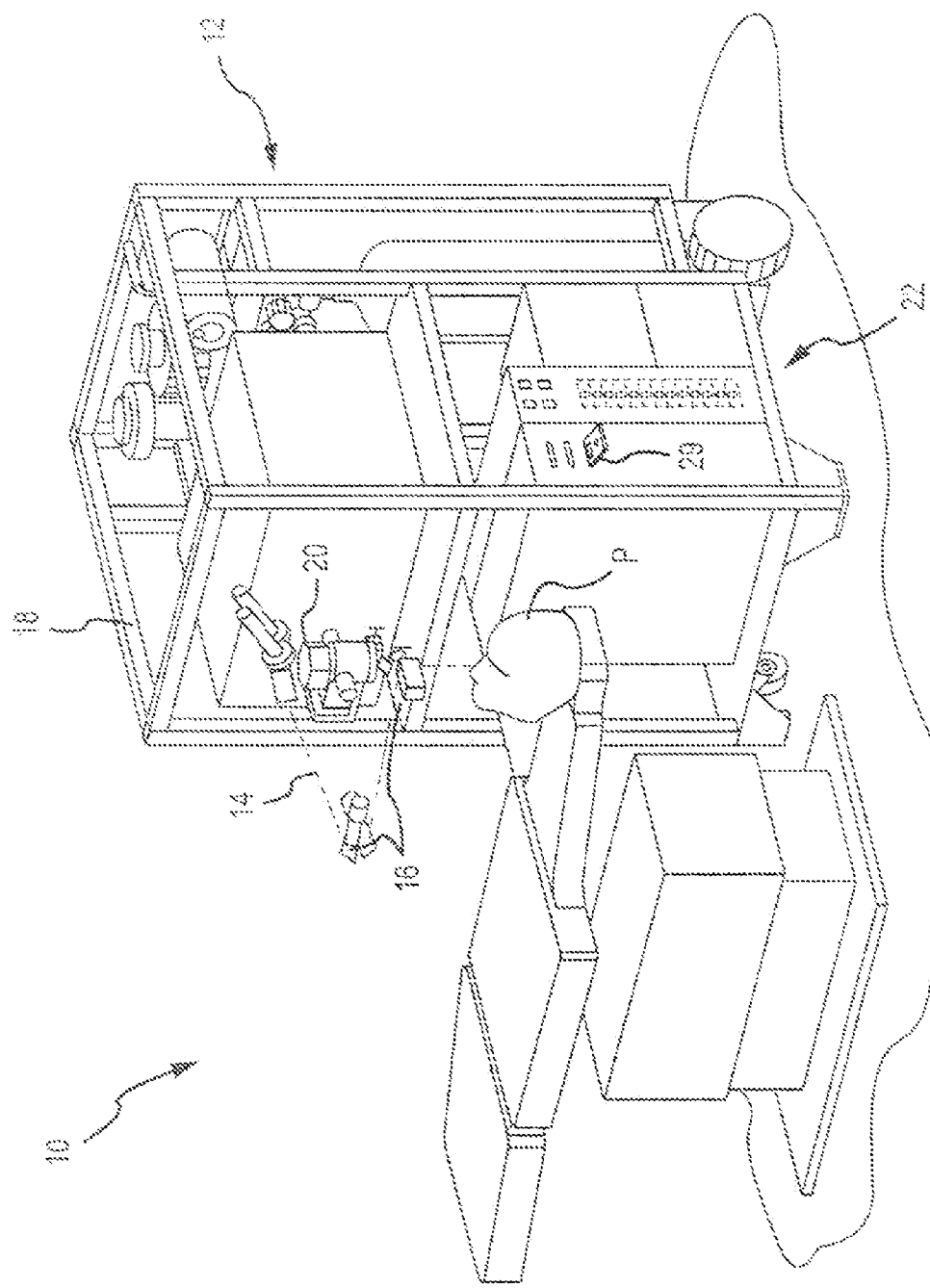
FIG. 1 illustrates a laser ablation system according to an embodiment of the present invention.

Embodiments of the present invention include systems and methods which use treatment table content (e.g. laser pulse instructions) to derive or generate an expected optical refraction, and compare that expected refraction with an intended refraction for the patient Typically, optical refractions include sphere, cylinder, and axis components. In addition to the treatment table laser instructions, the derived expected refraction may also take into account the treatment or vertex plane, for example to ensure that the derived refraction plane matches the intended refraction plane. Further, embodiments of the present invention provide systems and methods for treatment table validation that implement a separate, independent set of code to ensure that a planned refraction in the treatment table is consistent with the desired refraction. Thus, an exemplary method may involve inputting an intended refraction for a patient, inputting a treatment table containing laser ablation instructions, calculating an expected optical refraction based on the treatment table and optionally a vertex or treatment plane parameter, comparing the expected optical refraction with the intended refraction, and evaluating the treatment table based on the comparison of the expected optical refraction with the input refraction. If the expected optical refraction deviates significantly from the intended refraction, the treatment table will be disqualified.

In some cases, an intended optical refraction is dependent upon ophthalmic sphere, cylinder, and axis terms that are not based on Zernike values, whereas an expected optical refraction is dependent on sphere, cylinder, and axis terms that are based on Zernike values. Intended optical refractions, such as those dependent on ophthalmic sphere, cylinder, and axis terms, can be related to Zernikes (e.g. wavefront-guided), or physician input (e.g. VSS Refractive™ technique, non-wavefront guided, or manifest refraction). Optionally, wavefront-guided or nonwavefront-guided data can be used on conjunction with a physician adjustment.

Embodiments of the present invention can be readily adapted for use with existing laser systems, wavefront measurement systems, and other optical measurement devices. Although the systems, software, and methods of the present invention are described primarily in the context of a laser eye surgery system, it should be understood the present invention may be adapted for use in alternative eye treatment procedures, systems, or modalities, such as spectacle lenses, intraocular lenses, accommodating IOLs, contact lenses, corneal ring implants, collagenous corneal tissue thermal remodeling, corneal inlays, corneal onlays, other corneal implants or grafts, and the like. Relatedly, systems, software, and methods according to embodiments of the present invention are well suited for customizing any of these treatment modalities to a specific patient. Thus, for example, embodiments encompass custom intraocular lenses, custom contact lenses, custom corneal implants, and the like, which can be configured to treat or ameliorate any of a variety of vision conditions in a particular patient based on their unique ocular characteristics or anatomy. Aspects of techniques described herein can be implemented in a variety of laser and aberrometer devices, including without limitation the VISX WaveScan WaveFront® System and VISX STAR 54® Excimer Laser System, the Wavelight® Alegretto and Tscherning-based aberrometer; the Alcon Ladarvision® lasers and Ladarwave® aberrometer; the Bausch and Lomb Zyoptix® laser and related aberrometer, and the Zeiss® laser and WASCA® aberrometer.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with an input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 2:
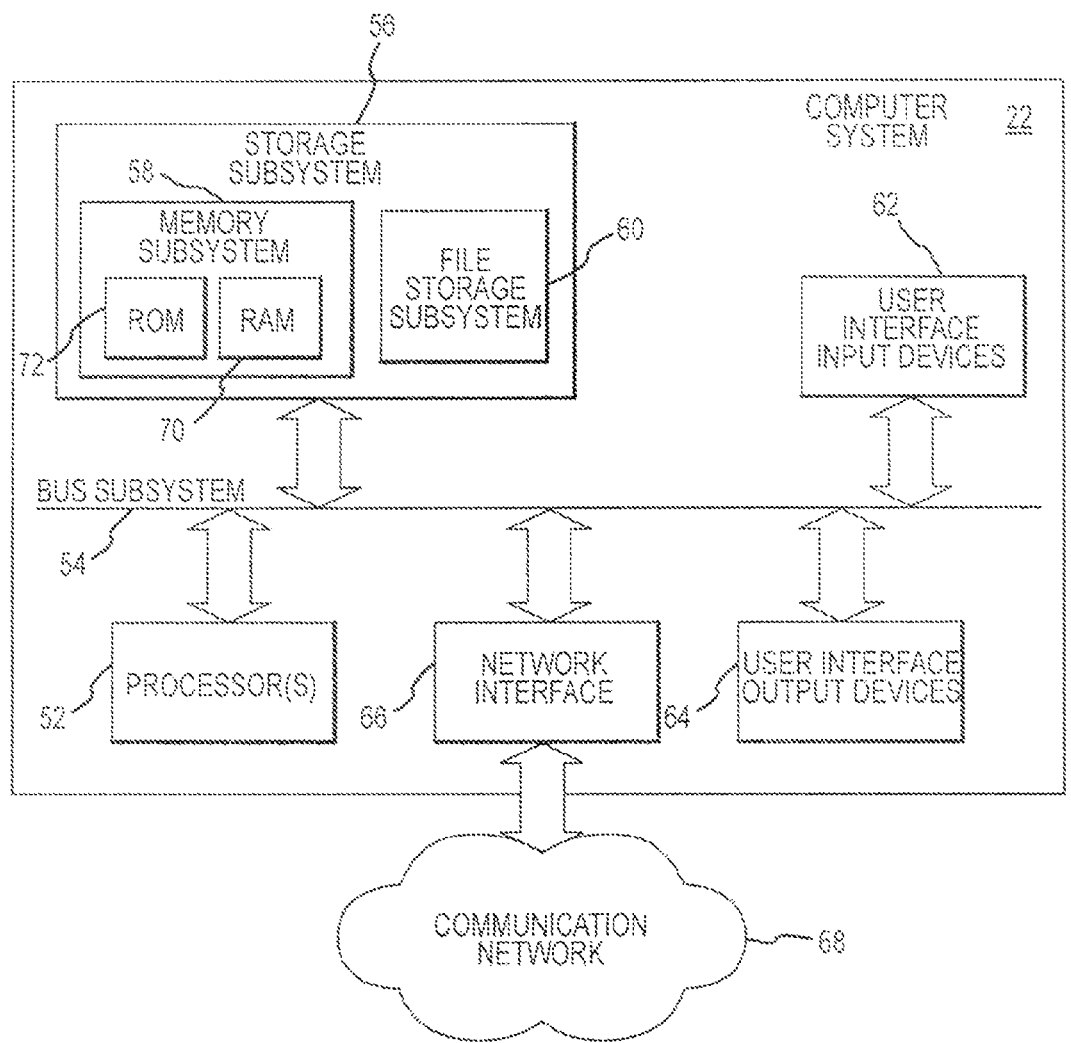
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
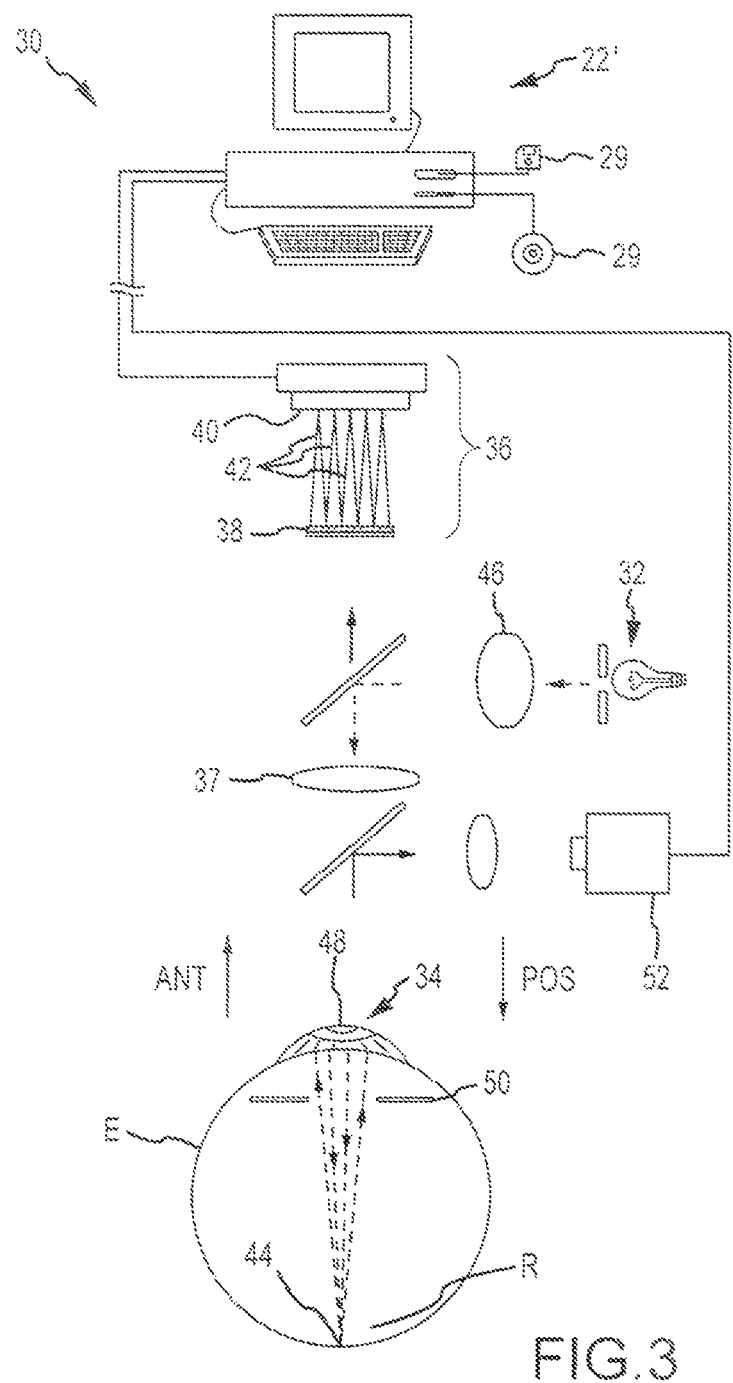
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
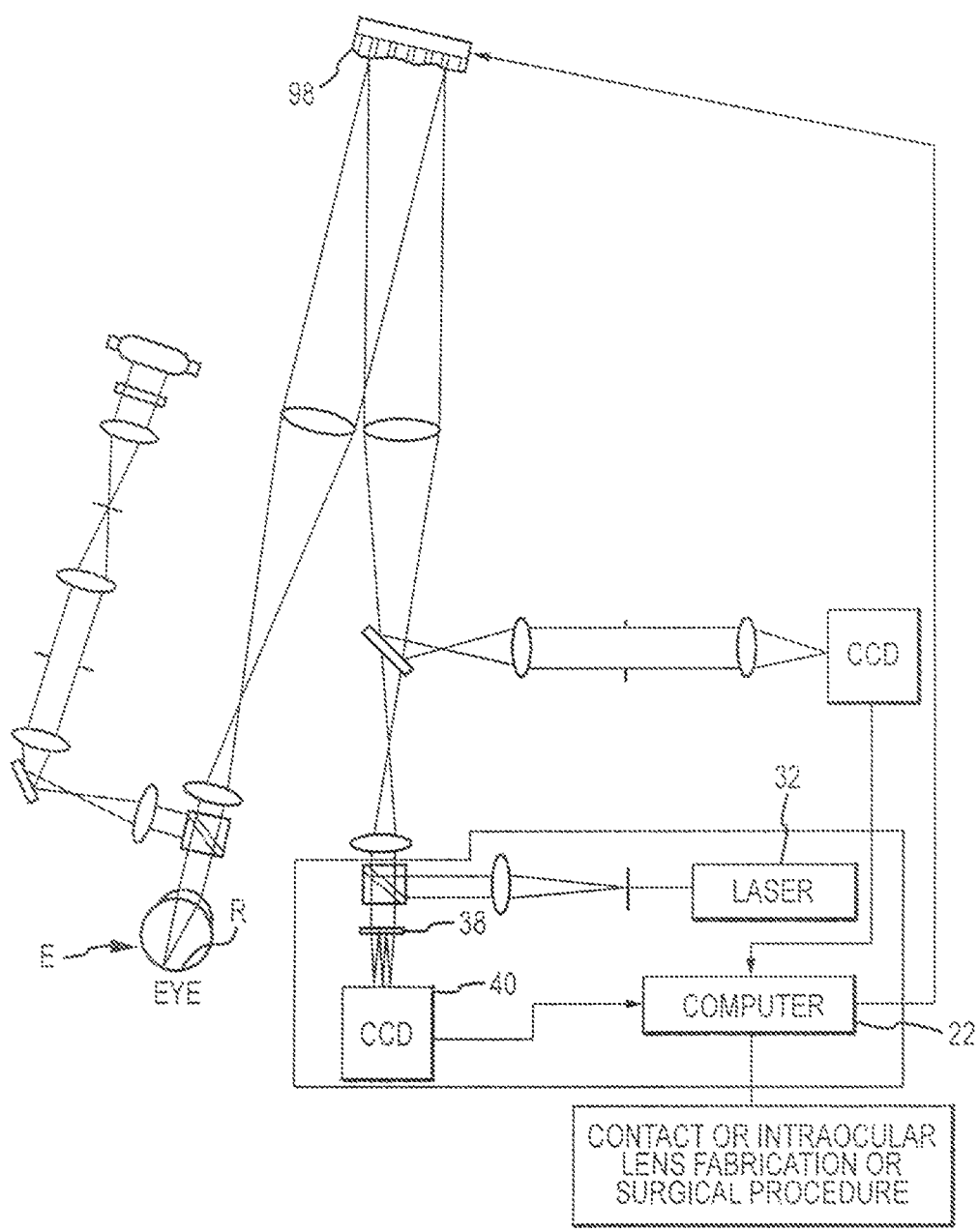
FIG. 3A illustrates another wavefront measurement system according to an embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a WaveScan® system, available from VISX, INCORPORATED of Santa Clara, Calif. One embodiment includes a WaveScan system with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with the present invention. Relatedly, embodiments of the present invention encompass the implementation of any of a variety of optical instruments provided by WaveFront Sciences, Inc., including the COAS wavefront aberrometer, the ClearWave contact lens aberrometer, the CrystalWave IOL aberrometer, and the like.

Figure 4:
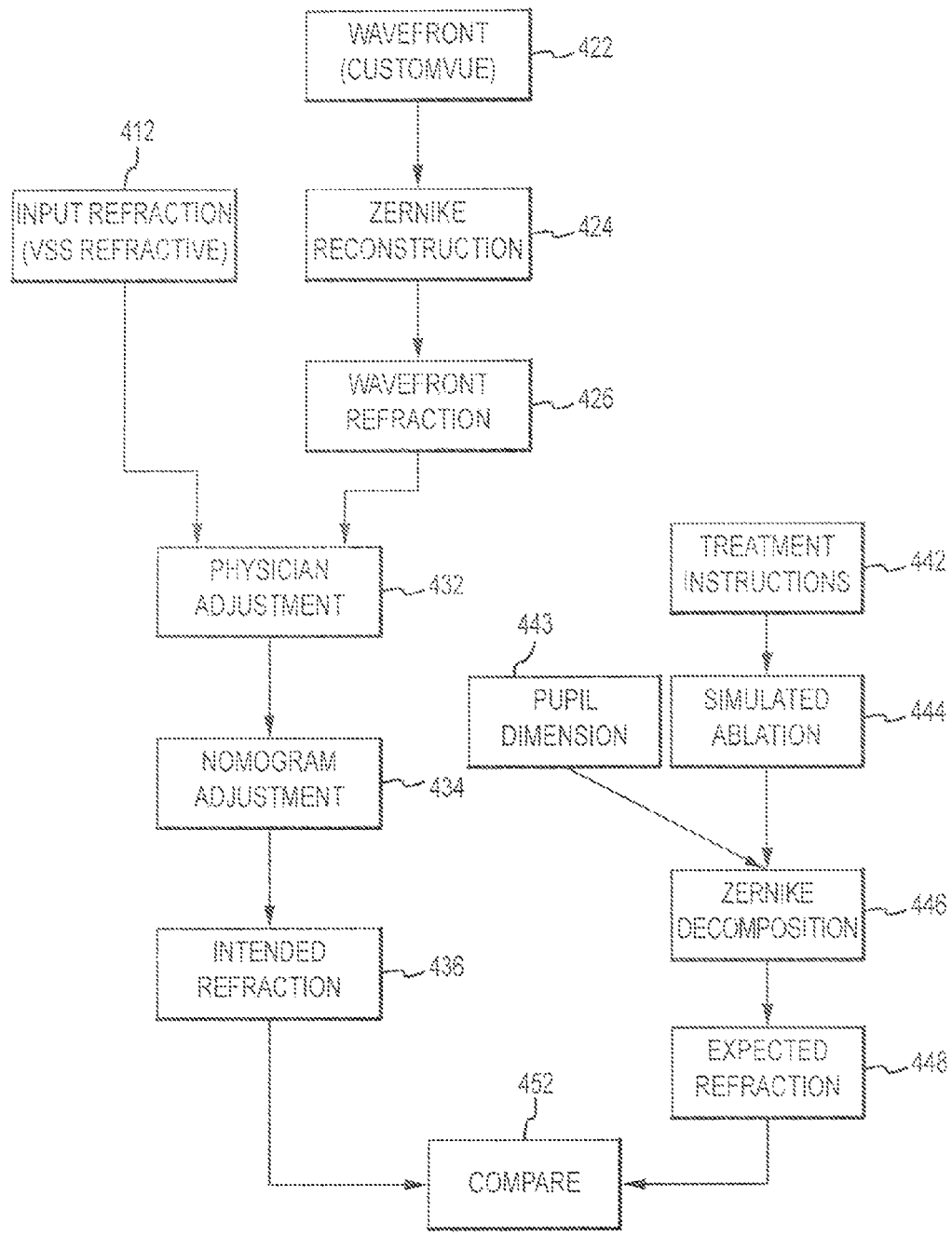
FIG. 4 shows aspects of an evaluation system according to embodiments of the present invention.

FIG. 4 depicts aspects of an evaluation system 400 according to embodiments of the present invention. As shown here, system 400 may include an Input Refraction module 412, a Wavefront module 422, a Zernike Reconstruction module 424, a Wavefront Refraction module 426, a Physician Adjustment module 432, a Nomogram Adjustment module 434, an Intended Refraction module 436, a Treatment Instructions module 442, a Pupil Dimension module 443, a Simulated Ablation module 444, a Zernike Decomposition module 446, an Expected Refraction module 448, and a Comparison module 452.

Input Refraction

The Input Refraction module 412 can operate to receive, process, and transmit information related to original refractions from the patient, such as VSS Refractive™ technology (Variable Spot Scanning) data, or manifest or subjective refraction. This information can correspond to non-wavefront guided data. According to some embodiments, Input Refraction module 412 can be configured to receive information regarding the refractive error of a patient. Such refractive error information may include sphere, cylinder, cylinder axis, and vertex distance data. Hence, low order aberration information can be used. For example, refractive error information may correspond to input cases such as myopia or hyperopia. In some cases, the refractive error information may be obtained at or correlated with a spectacle plane (e.g. 12.5 mm vertex). Input Refraction module 412 can also be configured to convert the input refractive error information to refractive error information relative to the corneal plane. Such plane conversion techniques are discussed in G.-m. Dai, Wavefront Optics for Vision Correction (SPIE Press, 2008), which is incorporated herein by reference. Plane conversion techniques can correspond to a vertex distance change or adjustment. Embodiments of the present invention encompass systems and methods for converting between treatment planes, user-defined or physician-defined planes, spectacle planes, corneal planes, pupil planes, and other planes of interest. Further, Input Refraction module 412 can be configured to output or transmit the corneal plane refractive error information, which may include sphere, cylinder, cylinder axis, and vertex distance components. In some cases, the refractive error information can be presented in the following format: sphere value DS/cylinder value DC×axis value @ vertex distance value. Optionally, Sphere and Cylinder can be represented in terms of diopters of power, Axis can be represented in terms of angle or degrees, and Vertex Distance can be represented in terms of millimeters. Sphere typically presents a measurement of lens power for myopia (negative) or hyperopia (positive), and cylinder typically presents a measurement of lens power for astigmatism. Hence, this refraction information and other eye measurements can be processed, as described herein, and compared with processed treatment table information to qualify the treatment table.

Wavefront

The Wavefront module 422 can operate to receive, process, and transmit information related to CustomVue™ technology or wavefront guided data. According to some embodiments, Wavefront module 422 can be configured to receive information regarding the wavefront error of a patient. Such wavefront error information may include wavefront map and wavefront diameter data. In some cases, the wavefront error information may be obtained at or correlated with a pupil plane. Wavefront module 422 can also be configured to process Hartmann-Shack spot diagram data, for example as described in G.-m. Dai, Wavefront Optics for Vision Correction (SPIE Press, 2008). Hartmann-Shack data can correspond to wavefront map data and wavefront diameter data. Typically, Hartmann-Shack data provides x and y shift information corresponding to array lenslets, and a wavefront data map can be derived from the Hartmann-Shack data. The map may optionally be associated with a particular wavefront diameter, particularly when the map is described with Zernike terms. In some cases, the map may be represented by a discrete matrix. Hence, Wavefront module 422 can be configured to output or transmit wavefront slope data, which may include x- and y-slope information.

Zernike Reconstruction

The Zernike Reconstruction module 424 can operate to receive information such as wavefront slope data, including for example x- and y-slope data. Zernike Reconstruction module 424 can also be configured to process the wavefront slope data with a Zernike reconstruction technique to obtain Zernike coefficient data, for example as described in G.-m. Dai, Wavefront Optics for Vision Correction (SPIE Press, 2008). Further, Zernike Reconstruction module 424 can be configured to output or transmit the Zernike coefficient information.

Wavefront Refraction

The Wavefront Refraction module 426 can operate to receive Zernike coefficient information, such as data related to z3, z4, and z5 Zernike coefficients. Wavefront Refraction module 426 can also be configured to receive wavefront diameter information. What is more, Wavefront Refraction module 426 can be configured to determine or calculate wavefront refraction information, for example based on Zernike coefficients and wavefront diameter, as discussed in G.-m. Dai, Wavefront Optics for Vision Correction (SPIE Press, 2008). The wavefront refraction information can be generated so as to correlated with a pupil plane, or with a corneal plane. Further, Wavefront Refraction module 426 can transmit or output the wavefront refraction information.

Physician Adjustment

The Physician Adjustment module 432 can be configured to receive information related to additional refractive correction at the user vertex or plane which may be selected or desired by a physician or operator. The selected plane can correspond to the pupil plane, the cornea plane, the spectacle plane, or some other user-defined plane. The Physician Adjustment can be applied at the selected or user-defined plane. For example, if the user vertex or plane corresponds to a spectacle plane, the physician can apply the adjustment at the spectacle plane as well. Hence, if the physician desired to add another diopter of treatment, the additional diopter could be applied at the spectacle plane when the physician is planning for a particular treatment. The adjustment is combined with the correction, and the combination can be converted to another plane, for example the corneal plane. Physician Adjustment module 432 can also be configured to convert the physician adjustment to the corneal plane, as described in G.-m. Dai, Wavefront Optics for Vision Correction (SPIE Press, 2008). Moreover, Physician Adjustment module 432 can be configured to transmit or output information relating the physician adjustment at the corneal plane. Such information corresponding to the corneal plane, or another selected plane, can be used for comparison and evaluation as discussed elsewhere herein.

Nomogram Adjustment

The Nomogram Adjustment module 434 can be configured to receive information related to a percentage of a treatment target multiplication factor. Nomogram Adjustment module 434 can also be configured to multiply the nomogram factor. The multiplication factor can be determined by the sum of one plus the nomogram adjustment percentage. For example, if the nomogram adjustment percentage is 8%, the multiplication factor can be calculated as one plus 8/100, or 1.08. According to some embodiments, the nomogram adjustment percentage can be a value within a range from about −10% to about +10%. Relatedly, according to some embodiments, the multiplication factor can be a value within a range from about 0.9 to about 1.1. Further, the Nomogram Adjustment module 434 can be configured to transmit or output information corresponding to a multiplied treatment target.

Intended Refraction

The Intended Refraction module 436 can operate to receive information directly from Wavefront Refraction module 426, or from Physician Adjustment module 432 or Nomogram Adjustment module 434. According to some embodiments, Intended Refraction module 436 can be configured to receive information that is similar to or the same as the input refraction discussed above in relation to the Input Refraction module 412. For example, Intended Refraction module 436 can be configured to receive information regarding the refractive error of a patient. Such refractive error information may include sphere, cylinder, cylinder axis, and vertex distance data. In some cases, the refractive error information may be obtained at or correlated with a spectacle plane. Typically, the refractive error information or intended refraction information is based on a correction that is planned for application to the patient's eye. Such intended or desired refractive correction information can also be represented in terms of ocular or optical refraction data. Intended Refraction module 436 can also be configured to convert the input refractive error information to refractive error information relative to the corneal plane. Such plane conversion techniques are discussed in G.-m. Dai, Wavefront Optics for Vision Correction (SPIE Press, 2008). Further, Intended Refraction module 436 can be configured to output or transmit the corneal plane refractive error information, which may include sphere, cylinder, cylinder axis, and vertex distance components. For example, Intended Refraction module 436 can be configured to transmit refractive information that is dependent upon or correlated with a sphere ophthalmic term, a cylinder ophthalmic term, and an axis ophthalmic term.

In some cases, the intended optical refraction can be related to Zernike terms, and in some cases the intended optical refraction can be related to manifest refraction which is used in VSS refractive. For example, the intended optical refraction can be dependent upon ophthalmic terms such as sphere, cylinder, and axis that are not directly related to Zernike terms. In some instances, the resolution of a wavefront aberrometer device may be greater than that of a phoropter device. Hence, a patient receiving a wavefront aberrometer exam that provides a result of 3.75 diopters, may also receive a phoropter exam that provides a result of 3.50 diopters. Either of the wavefront or manifest refraction results may be used.

Treatment Instructions

The Treatment Instructions module 442 can be configured to receive information related to a treatment target. Further, Treatment Instructions module 442 can operate to process the treatment target information according to a simulated annealing least squares algorithm (SALSA) to obtain a treatment table or set of laser ablation instructions for a patient, as described in G.-m. Dai, Wavefront Optics for Vision Correction (SPIE Press, 2008). The treatment table may include laser instruction parameters such as iris size, x- and y-scanning positions or locations, shot-to-shot or beam pulse delay time, pulse or beam size, and other ablation instruction parameters. The laser parameters can be used to deliver an ablation that corresponds to the Zernike polynomial terms, or other basis function terms such as Seidel series terms. A refraction typically corresponds to a second order polynomial, and basis functions such as Zernike polynomials and Seidel series are well suited for characterizing refractions based on calculation of second order coefficients. Treatment Instructions module 442 may also be configured to transmit or output laser ablation instructions, such as iris size, x- and y-scanning positions, shot-to-shot delay time, and the like. The treatment table may characterize information that has been processed via a table generation engine. When the ablation is simulated based on the ensemble of laser instructions, the resulting volumetric information corresponds to the Zernike terms.

Pupil Dimension

The Pupil Dimension module 443 can operate to process information related to a pupil dimension of the patient. In some cases, Pupil Dimension module 443 can be configured to receive a selected wavefront or pupil diameter, and to calculate a refraction corresponding to the pupil dimension. Such information can be transmitted to a Zernike Decomposition module, as discussed elsewhere herein. In some cases, a pupil diameter can correspond with a wavefront diameter used during a wavefront exam, for example a wavefront exam which may be performed in conjunction with the operation of Wavefront module 422. The pupil dimension may in some instances have a value within a range from about 3 mm to about 7 mm. In some cases, the pupil dimension is a pupil diameter of about 4 mm. Hence, embodiments encompass techniques that calculate a refraction over a 4 mm pupil diameter, as well as other pupil dimensions. Exemplary aspects of pupil dimension selection are discussed in U.S. Pat. No. 7,460,288, which is incorporated herein by reference.

Simulated Ablation

The Simulated Ablation module 444 can be configured to receive information related to laser ablation instructions, such as iris size, x- and y-scanning positions or tracking distances, shot-to-shot delay time, and the like. Simulated Ablation module 444 can also be configured to process information related to a simulated laser ablation or laser ablation instructions to obtain a simulated volume or tissue volume planned for removal, based on basis data. Often, specific basis data information is available for corresponding specific iris sizes. Hence, for each particular iris size there can be a corresponding basis data information. Further, Simulated Ablation module 444 can be configured to output or transmit the simulated volume or tissue volume intended to be removed.

Zernike Decomposition

The Zernike Decomposition module 446 can be configured to receive information related to a pupil dimension and a tissue volume being removed. Zernike Decomposition module 446 can also be configured to process the pupil dimension and tissue volume information according to a singular value decomposition method to obtain Zernike coefficient and wavefront diameter information. In some cases, Zernike Decomposition module 446 generates data related to a set of second radial order Zernike polynomial terms. The second order Zernike polynomials, z3 z4, and z5 are analytically related to sphere, cylinder, and axis. The group of z3 z4, and z5 terms can be used to determine sphere. Similarly, the group of z3 z4, and z5 terms can be used to determine cylinder. Further, the group of z3 z4, and z5 terms can be used to determine axis. Aspects of a singular value decomposition method are discussed in G.-m. Dai, Wavefront Optics for Vision Correction (SPIE Press, 2008). Further, Zernike Decomposition module 446 can be configured to transmit or output information related to the Zernike coefficients and wavefront diameter. As discussed elsewhere herein, embodiments may encompass techniques that involve other basis function coefficients or second order radial polynomials, for example Seidel power series.

Expected Refraction

The Expected Refraction module 448 can be configured to receive information regarding Zernike coefficients (e.g. z3, z4, and z5 terms) and a pupil dimension. Expected Refraction module 448 can be configured to determine a wavefront refraction based on the Zernike coefficient and pupil dimension information. Aspects of a wavefront refraction determination are discussed in G.-m. Dai, Wavefront Optics for Vision Correction (SPIE Press, 2008). Further, Expected Refraction module 448 can be configured to transmit or output information related to an expected optical refraction for the patient, which may include for example a sphere ophthalmic term characterized by a set of second radial order Zernike polynomial terms, a cylinder ophthalmic term characterized by the set of second radial order Zernike polynomial terms, and an axis ophthalmic term characterized by the set of second radial order Zernike polynomial terms. Optical refraction information typically corresponds to second order wavefront data or low order aberrations, and is distinctly different from a surface shape, height, or topography. For example, when piston is added, the surface shape changes, however the curvature or refraction does not. Similarly, if a surface is tilted, the surface changes, however the curvature or refraction does not. Piston corresponds to a zero order Zernike polynomial, and represents upward or downward displacement of a wavefront. Relatedly, tilt corresponds to a first order Zernike polynomial.

Comparison

The Comparison module 452 can operate to compare intended refraction information with expected optical refraction information. For example, intended spherical equivalent (which corresponds to sphere and cylinder) can be compared with expected spherical equivalent, intended cylinder can be compared with expected cylinder, and intended axis can be compared with expected axis. In some cases, Comparison module 452 can be configured to receive information regarding an intended refraction and an expected or achieved refraction, optionally adjusted to or characterized in terms of a common or user-defined plane such as the corneal plane, pupil plane, or spectacle plane.

Because refractions are typically dependent upon the vertex plane, it may be desirable to compare intended and expected optical refraction information that corresponds to a common or specific vertex plane. Exemplary vertex or refraction conversions which may be used are described in U.S. Pat. No. 7,296,893, incorporated herein by reference. Hence, if the input refraction data corresponds to the spectacle plane, and the wavefront data corresponds to the pupil plane, embodiments of the present invention encompass techniques for converting this data so that it may be compared with data corresponding to a common plane, such as the corneal plane. Comparison module 452 can also be configured to compare the intended refraction and expected optical refraction information. For example, Comparison module 452 can operate to determine an algebraic difference for the sphere, cylinder, and axis ophthalmic terms, and compare the differences with a tolerance for the ophthalmic term. Comparison module 452 can also be configured to qualify or disqualify a treatment table based on the comparison between the respective refraction differences and tolerances.

Typically, comparison module 452 operates to compare low order aberration information related to the intended refraction with low order aberration information related to the expected refraction. Embodiments of the present invention also encompass techniques that involve the comparison of high order aberration information related to the intended refraction with high order aberration information related to the expected refraction.

High order aberrations encompass, for example, third order aberrations including trefoil and coma, as well as fourth order aberrations including $Z(4, -4)$, $Z(4, -2)$, spherical aberration, $Z(4,2)$, and $Z(4,4)$ errors. Generally, high order aberrations include third order errors and above.

Hence, comparison techniques can involve comparing an expected optical refraction for the patient, which is based on a pupil dimension and a simulated ablation, with an intended optical refraction for the patient. The expected optical refraction can be dependent on a sphere ophthalmic term characterized by a set of second radial order Zernike polynomial terms, a cylinder ophthalmic term characterized by the set of second radial order Zernike polynomial terms, and an axis ophthalmic term characterized by the set of second radial order Zernike polynomial terms. The expected optical refraction profile can also be independent of a piston ophthalmic term characterized by a zero radial order Zernike polynomial term, an x-tilt ophthalmic term characterized by a set of first radial order Zernike polynomial terms, and a y-tilt ophthalmic term characterized by the set of first radial order Zernike polynomial terms. The intended optical refraction for the patient can be dependent on a sphere ophthalmic term, a cylinder ophthalmic term, and an axis ophthalmic term. Further, the intended optical refraction profile can be independent of a piston ophthalmic term, an x-tilt ophthalmic term, and a y-tilt ophthalmic term.

Scaling

With continued reference to FIG. 4, evaluation techniques can be implemented in various ways. For example, in a VSS refractive treatment, an evaluation technique may be implemented by using a scaling factor to scale down the refraction from the treatment table, without using a scaling factor to boost the treatment target. Such approaches are well suited for use with a Munnerlyn shape which is deeper than a parabolic shape. Relatedly, in a CustomVue® treatment, an evaluation technique may be implemented by using a scaling factor, for example of 1.11, to boost the treatment target, without using a scaling factor to scale down the refraction from the treatment table, for example without a parabolic or Munnerlyn scaling. With regard to the VSS technique, scaling can be applied in a linear fashion, to a Munnerlyn or parabolic shape. In some case, a Munnerlyn shape can be scaled so as to approach or approximate a parabolic shape. A parabolic shape represents a second order shape, and a Munnerlyn represents a second order shape as supplemented with higher orders. Hence, for the same refraction, a Munnerlyn shape and a parabolic shape can differ. A comparison can be performed either at the corneal plane or at the vertex plane, or both. According to some embodiments, the treatment table should qualify or pass if the difference between the refraction from the table and the initial input refraction is smaller than the criteria used for wavefront exam selection during the treatment table creation phase. In some cases, embodiments of the present invention provide systems and methods for qualifying a VSS refractive treatment. Exemplary techniques can implement a treatment qualification validation process whereby a refraction from a simulated tissue ablation is compared with an input refraction, for example to ensure that no abnormal tables have been created. Because the Munnerlyn shape and a parabolic shape may differ, it may be useful to convert a Munnerlyn refraction to a parabolic refraction. Munnerlyn shapes are discussed generally at C. R. Munnerlyn, S. J. Koons, and J. Marshall, "Photorefractive keratectomy: A technique for laser refractive surgery," *J. Cataract Refract. Surg.* 14, 46-52 (1988), the entire content of which is incorporated herein by reference. Embodiments of the present invention encompass different types of scaling. For example, the techniques disclosed herein may include refraction scaling or shape scaling, both of which involve multiplication. In some cases, it is possible to use scaling factors of 1.015 for myopic sphere, 1.025 for hyperopic sphere, and 1.015 for cylinder to scale a refraction, for example as discussed in relation to Eqs. (9) to (11) provided elsewhere herein. In some cases, it is possible to use a scaling factor of 1.11 to scale a shape.

Figure 4A:
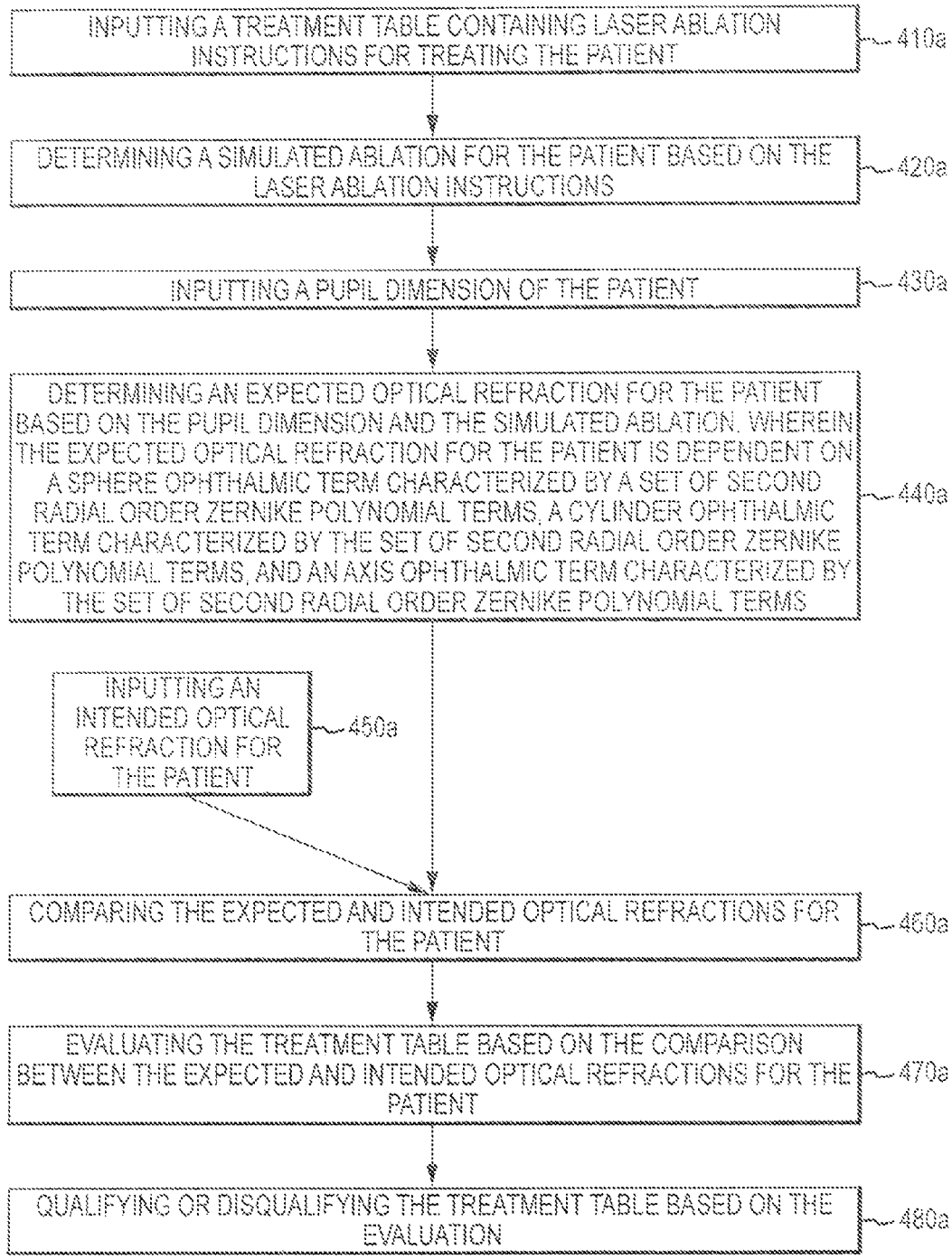
FIG. 4A depicts aspects of an evaluation method according to embodiments of the present invention.

FIG. 4A illustrates an exemplary method 400a of evaluating a treatment table for use in an ophthalmologic refractive surgery for a patient. As shown here, such evaluation, verification, or qualification techniques may include inputting a treatment table containing laser ablation instructions for treating the patient, as depicted by step 410a. Methods may also include determining a simulated ablation for the patient based on the laser ablation instructions as indicated by step 420a, and inputting a pupil dimension of the patient as indicated by step 430a. In an exemplary embodiment, an evaluation method may include determining an expected optical refraction for the patient based on the pupil dimension and the simulated ablations, as indicated by step 440a, wherein the expected optical refraction for the patient is dependent on a sphere ophthalmic term characterized by a set of second radial order Zernike polynomial terms, a cylinder ophthalmic term characterized by the set of second radial order Zernike polynomial terms, and an axis ophthalmic term characterized by the set of second radial order Zernike polynomial terms. Optionally, the expected optical refraction profile can be independent of a piston ophthalmic term characterized by a zero radial order Zernike polynomial term, an x-tilt ophthalmic term characterized by a set of first radial order Zernike polynomial terms, and a y-tilt ophthalmic term characterized by the set of first radial order Zernike polynomial terms. Method embodiments may also include inputting an intended optical refraction for the patient, as indicated by step 450a, wherein the intended optical refraction for the patient is dependent on a sphere ophthalmic term, a cylinder ophthalmic term, and an axis ophthalmic term, and wherein the intended optical refraction profile is independent of a piston ophthalmic term, an x-tilt ophthalmic term, and a y-tilt ophthalmic term. Further, methods may include comparing the expected and intended optical refractions for the patient, as indicated by step 460a. The refractions can be adjusted to or correlated with a common plane, such as the treatment plane, pupil plane, corneal plane, or spectacle plane, prior to the comparison. In some cases, methods may include evaluating the treatment table based on the comparison between the expected and intended optical refractions for the patient, as indicated by step 470a, and qualifying or disqualifying the treatment table based on the evaluation, as indicated by step 480a. For example, evaluation methods may include determining a difference between the intended optical refraction and the expected optical refraction, and comparing that difference to a predefined tolerance. If the difference between the intended optical refraction and the expected optical refraction is within the tolerance, the method may include qualifying or passing the treatment table, or otherwise approving the treatment table for use. Such qualification techniques can provide an enhanced level of safety during a patient treatment, for example by helping to ensure that a treatment table has not been altered or hacked.

Information corresponding to any of a variety of inputs may be processed, such as data related to a spectacle plane parameter, a corneal plane, a pupil plane, or any other desired vertex plane or distance parameter.

Figure 5:
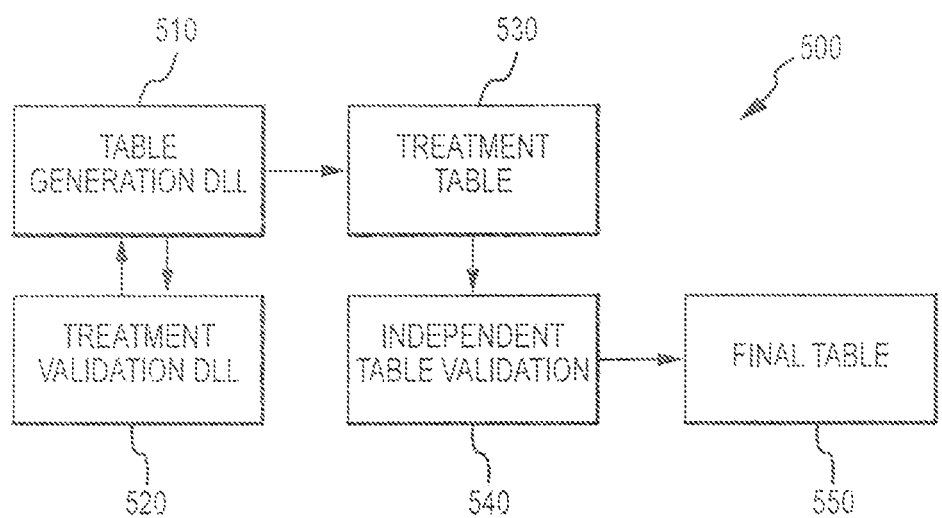
FIG. 5 shows aspects of an evaluation system according to embodiments of the present invention.

FIG. 5 depicts aspects of an evaluation system 500 according to embodiments of the present invention. As shown here, system 500 may include a Table Generation DLL module 510, a Treatment Validation DLL module 520, a Treatment Table module 530, an Independent Table Validation module 540, and a Final Table module 550.

As shown here, for a Table Generation DLL 510 or treatment generation engine, a validation process can be performed by a Treatment Validation DLL 520 whereby a validation is conducted for various possible simulation annealing solutions. Moreover, a process to validate a ready-to-use treatment corresponding to Treatment Table 530 can provide a separate, independent step for validating a treatment table. Such an independent validation technique can operate separately from a treatment table generation engine or a treatment table generation algorithm which may involve a simulated annealing process, and therefore does not incorporate possible error which may result, for example, due to unexpected error from third-party DLLs, from mal-operation of the users that is not captured in the fault tree analysis during the software design phase, or from other possible sources of error. For example, due to possible unknown bugs or errors in the high level software code or embedded in third-party libraries (DLLs), or due to inappropriate operation of the software, it is possible that a software that is verified and validated by Treatment Validation DLL 520 may still produce an unwanted treatment table that can potentially result in a suboptimal treatment. Hence, embodiments of the present invention encompass validation techniques for addressing situations where third party components such as operating systems, computers, or DLL's introduce error or are malfunctioning, and other sources that introduce unforeseeable or incorrect results.

According to some embodiments, the validation of a treatment table can be implemented in connection with the table generation system or software. In some cases, the validation of a treatment table can be implemented in connection with the laser system or software, such as validation software residing in the laser system. For instance, a VSS-based validation as described elsewhere herein, which may optionally be in relation with an aberrometer or wavefront system, can also be implemented in a laser system. Hence, it is possible to validate a treatment table after it is generated and saved, and it is also possible to validate a treatment table prior to use in treating a patient. Hence, if a treatment table has been corrupted for some reason, validation and qualification can be performed prior to laser delivery of the ablation pulses, and the treatment can be canceled if disqualification is appropriate.

According to some embodiments, the validation of a treatment table can be implemented in connection with software residing in a diagnostic device such as WaveScan® and iDesign™ devices. System and method embodiments disclosed herein can also be configured to validate treatment tables for topographic driven treatment, refraction driven or conventional treatment, and wavefront driven treatment.

Table Generation DLL module 510 can operate to process information related to treatment table generation, Treatment Validation DLL module 520 can operate to process information related to treatment validation, Treatment Table module 530 can operate to process information related to a treatment table, and Table Validation module 540 can operate to process information related to table validation. In some instances, Table Validation module 540 is configured to embody or implement techniques described elsewhere herein in relation to Comparison module 452. Final Table module 550 can operate to process information related to a final table. According to some embodiments, a final table corresponding to Final Table module 550 will be the same as a treatment table corresponding to Treatment Table module 530, in the event that the treatment table corresponding to Treatment Table module 530 is validated or qualified by Table Validation module 540.

Passing Criteria for Treatment Table Qualification

Any of a variety of exam selection criteria can be used to qualify a treatment table generated by the VSS Refractive™ technique. Numerous Monte Carlo simulations have been performed which support the suitability of such exam selection criteria for treatment table qualification.

According to some embodiments, the difference in spherical equivalent (SE), cylinder, and cylinder angle can be set or predetermined to satisfy the following qualification conditions.

$$|dSE|=|dS+0.5dC|=|S_1-S_0+0.5C_1-0.5C_0|<0.625 \quad (1)$$

$$|dC|=|C_1-C_0|\leq 0.5 \quad (2)$$

$$|dA|\leq 1.1538(|C_0|+|C_1|)/2+15.577 \text{ (for } |C_0|0.5 \text{ and } |C_1|>0.5, \text{ or ignore)} \quad (3)$$

As described here, Eq. 1 represents a comparison or difference between spherical equivalent, Eq. 2 represents a comparison or difference between cylinder, and Eq. 3 represents a comparison or difference between axis.

For example, if $C_0=0.55$ D, $C_1=0.5$ D, then according to Eq. 1, the cylinder difference is less than 0.5, and thus there may be no need to check cylinder angle. For another example, if $C_0=0.9$ D, $C_1=0.8$ D, then dA must be smaller than 14.6 degree in order to qualify. Also note that for Eq. (2), it is generally desirable that both use the same cylinder notation before the difference can be taken. For example, it is desirable that both $C_0$ and $C_1$ be positive, or that both $C_0$ and $C_1$ be negative.

Evaluation and Monte Carlo Simulation

Treatment qualification systems and methods according to embodiments of the present invention can be implemented in a variety of ways. There is typically inter-correlation between sphere and cylinder as well as the vertex correction. A scaling factor between a Munnerlyn power and a parabolic power may in some cases depend not only upon the sphere refraction, but also upon on the cylinder refraction. As described in G.-m. Dai, *Wavefront Optics for Vision Correction* (SPIE Press, 2008), the Munnerlyn shape may differ from a parabolic shape. For example, as described at page 90, supra, the Munnerlyn shape can be 11% deeper than parabolic shape, when a spherical myopia is considered.

Embodiments of the present invention encompass empirically adjusted and theoretically based systems and methods for implementing a treatment qualification technique. Such approaches can include processing a set of input refractions (e.g. with sphere between −15 D and +7 D and cylinder between −6 D and +6 D) with Munnerlyn shapes, decomposing the data into Zernike polynomials. Zernike decomposition may involve processing pupil dimension and tissue volume information to obtain Zernike coefficient and wavefront diameter information, such as data related to a set of second radial order Zernike polynomial terms, and determining the refractions based on the Zernike information. In this way, it is possible to determine an expected refraction, based on the Zernike coefficient and pupil dimension information.

Further, these approaches can include regressing the input Munnerlyn refraction against a calculated parabolic refraction using multivariate linear and quadratic parameters to obtain theoretical scaling factors for both sphere and cylinder. Still further, these approaches can include using a theoretical algorithm to test in a full implementation with vertex correction, cosine effect using random keratometry values, and the like, using Monte Carlo simulation with multiple (e.g. 5000) samples. Moreover, these approaches can include refining the theoretical algorithm based on the Monte Carlo simulation. What is more, these approaches can include retesting the revised algorithm for a new set of Monte Carlo simulation with multiple (e.g. 5000) samples. According to some embodiments, such approaches may be implemented in a production software.

The following formulas give an algorithm for sphere ($f_s$) and cylinder ($f_c$) scaling:

$$f_s=1.028-0.00275S-0.00448C \; (S<0) \quad (4)$$

$$f_s=1.028-0.00326S-0.00018C \; (S\geq 0) \quad (5)$$

$$f_c=1.011-0.005745S-0.00142C \quad (6)$$

As indicated here, both S and C can be refractions on the corneal plane. In some cases, it may be desirable to convert the input refractions on vertex plane to the corneal plane before these equations are used. Supposing the refractions on the vertex plane are $S_0$ and $C_0$, respectively, it is possible to write:

$$S = \frac{S_0}{1-0.001S_0 d} \quad (7)$$

$$C = \frac{S_0+C_0}{1-0.001(S_0+C_0)d} - S \quad (8)$$

When $f_s$ and $f_c$ are calculated, they can be applied to refractions on the corneal plane. For example, suppose the input refractions are −15 DS/−5.75 DC×64 @ 12.5 mm vertex. They are used to generate the Munnerlyn shape, which has more power than the corresponding parabolic shape. From Equations (7) and (8), it is possible to obtain the refractions on the corneal plane as −12.63 DS/−3.84 DC×64 @ 0 mm vertex.

Using Equations (4) and (6), it is possible to obtain $f_s=1.0799$ and $f_c=1.0889$. These are scaling factors which may be determined via Monte Carlo simulation. Further, such scaling factors can be applied to an input refraction. It can be assumed that the Zernike decomposed refractions from the treatment table are −13.68 DS/−4.09 DC×64 @ 0 mm vertex.

According to some embodiments, for the CustomVue® technique or Wavefront input data, there may be no need to use a scaling factor for refractions, however it may be beneficial to scale the treatment shape 11% to achieve a similar target depth corresponding to that of conventional or VSS Refractive™ input data.

The scaling factors for these refractions can be applied to obtain −12.67 DS/−3.76 DC×64 @ 0 mm vertex, which may correspond to a scaled refraction on the treatment plane or corneal plane. It is possible to convert these refractions to a 12.5 mm vertex using Equations (7) and (8), setting d=−12.5 mm. Such conversion corresponds to propagation to the spectacle plane. Hence, −12.67 DS/−3.76 DC×64 @ 0 mm vertex propagated to the spectacle plane is −15.05 DS/−5.62 DC×64 @ 12.5 mm vertex. Conversions are useful when comparing refractions, such as an intended refraction and an expected refraction, and this example illustrates that it is possible to compare refractions in, for example, a user vertex (e.g. spectacle) plane. Hence, a treatment table power of −13.68/−4.09×64 at 0 mm vertex can be vertex corrected to obtain the refraction as −15.05 DS/−5.62 DC×64 at 12.5 mm vertex. This leaves a residual error of −0.05 DS/0.13 DC.

The difference in SE can be calculated as (−15.05−5.62/2+15+5.75/2)=0.02 D, the difference in Cylinder can be calculated as −5.62+5.75=0.07 D, and the difference in axis can be calculated as 0. If the tolerance for SE is 0.625 D and the tolerance for cylinder is 0.5 D, then these SE and Cylinder values are within the tolerances, and hence the treatment can be approved for release to treat the patient.

Figure 6:
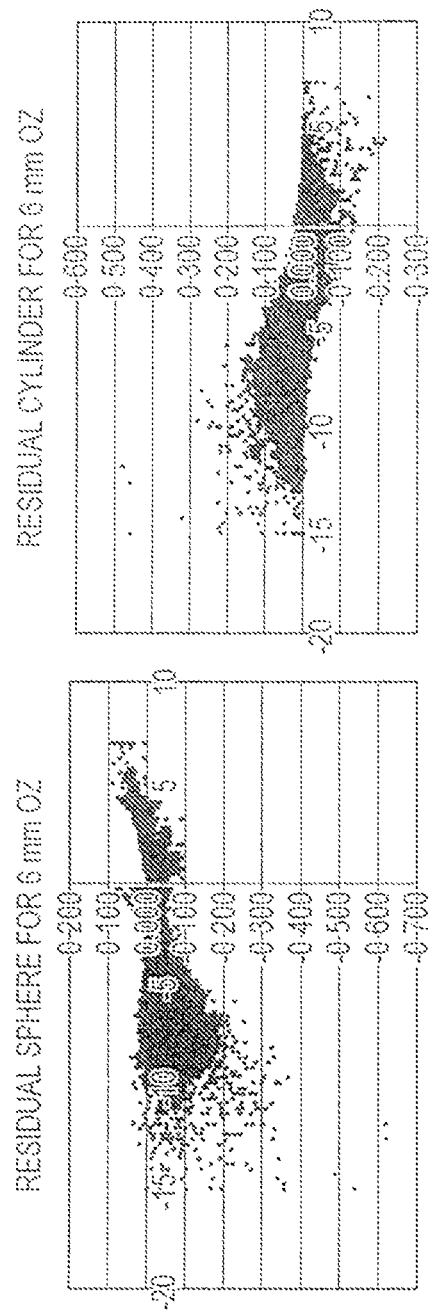
FIG. 6 illustrates aspects of residual error according to embodiments of the present invention.

FIG. 6 shows a residual error for 5000 simulated cases with 6 mm OZ. The left panel shows residual sphere, and the right panel shows residual cylinder, after correction of the scaling factors for 5000 simulated realistic cases. If the four outliers are excluded, the spread of sphere is within (−0.4 D, +0.1 D) and that of cylinder is within (−0.2 D, +0.3 D), both are in about half a diopter range. Without the exclusion, the range is still within the criteria listed in Eqs. (1) to (3).

Table 1 provides the residual error or residual refractions (in diopters) from a Monte Carlo simulation after implementing the algorithm shown in Eqs. (4) to (6), for optical zones of 7 mm, 6 mm, 5 mm, and 4 mm.

TABLE 1

| | OZ | | | | | | | |
|---|---|---|---|---|---|---|---|---|
| | 7 (mm) | | 6 (mm) | | 5 (mm) | | 4 (mm) | |
| | | | | Rx | | | | |
| | Sphere | Cylinder | Sphere | Cylinder | Sphere | Cylinder | Sphere | Cylinder |
| N | 5000 | 5000 | 5000 | 5000 | 5000 | 5000 | 5000 | 5000 |
| Mean | −0.043 | 0.015 | −0.043 | 0.014 | −0.045 | 0.016 | −0.013 | 0.017 |
| Stdev | 0.054 | 0.044 | 0.054 | 0.044 | 0.057 | 0.047 | 0.045 | 0.035 |
| Max | 0.206 | 0.480 | 0.090 | 0.476 | 0.149 | 0.432 | 0.132 | 0.265 |
| Min | −0.564 | −0.330 | −0.622 | −0.215 | −0.610 | 0.245 | −0.376 | −0.171 |

For the criteria for treatment table qualification, because the residual errors shown in Table 1 are within the exam selection criteria, it may be desirable to use the exam selection criteria to qualify treatment tables in terms of the refraction check. Embodiments of the present invention encompass techniques for qualifying an exam, which may involve the application of treatment table qualification criteria, and selecting the exam for treatment generation, which may involve the application of exam selection criteria.

Verification with Production Code and Revised Formulas

Eqs. (4) to (6) were implemented in a production code, and tested with about 1000 cases with each pupil sizes of 4 mm, 5 mm, 6 mm, and 7 mm. Occasional discrepancies were discovered, and it was determined that such discrepancies may be due to some implementation differences between the C++ code and the Matlab code. Subsequently, a set of new examples were generated and regression ran. Results for the new examples were much more linear, and the nonlinear behavior previously observed was absent.

Table 2 shows the linear factor for different pupil sizes. Scaling factor data for sphere $(f_s)$ and cylinder $(f_c)$ was regressed from data obtained with the production code for various pupil sizes.

TABLE 2

| Pupil | Minus Sph | Plus Sph | Cylinder |
|---|---|---|---|
| 4 mm | 0.999 | 1.022 | 1.010 |
| 5 mm | 1.014 | 1.037 | 1.023 |
| 6 mm | 1.026 | 1.026 | 1.014 |
| 7 mm | 1.023 | 1.014 | 1.014 |
| Average | 1.015 | 1.025 | 1.015 |

Based on the information in Table 2, the original Eqs. (4) to (6) were adjusted as follows. These equations can override equations (4)-(6).

$$f_s = 1.015 \ (S<0) \tag{9}$$

$$f_s = 1.025 \ (S \geq 0) \tag{10}$$

$$f_c = 1.015 \tag{11}$$

Figure 7:
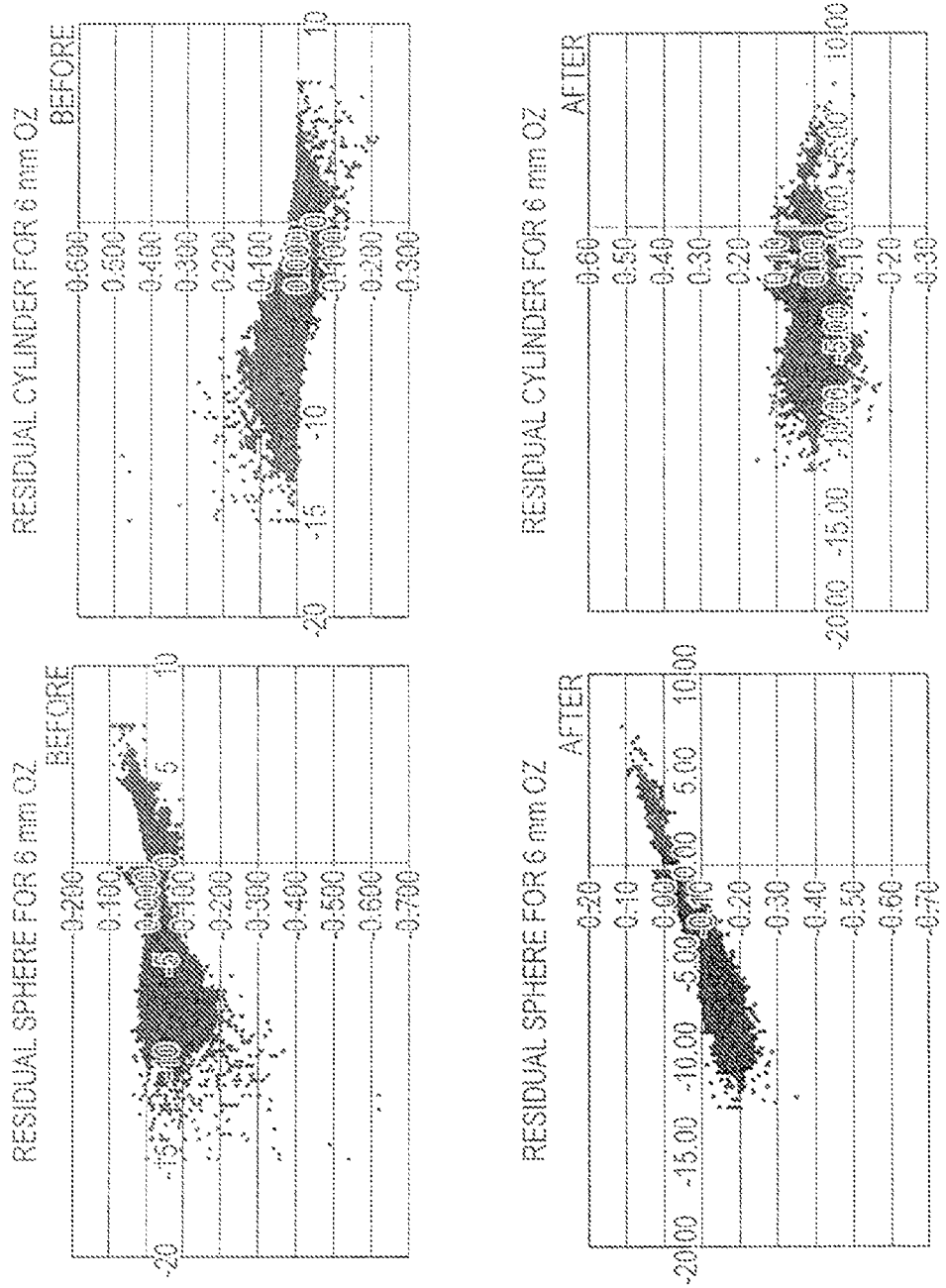
FIG. 7 illustrates aspects of residual sphere and cylinder according to embodiments of the present invention.

As a verification that this new implementation narrows the spread of the residual error both in sphere and cylinder, the same 5000 samples for each pupil which were used before, were again used running with the production code. This is the revised code based on the adjustments described above. FIG. 7 shows the results obtained for a 6 mm pupil using the revised code, compared with the previous results obtained using the original code. Specifically, the upper panels of FIG. 7 show the residual sphere (left panel) and residual cylinder (right panel) for a 6 mm pupil after correction of the scaling factors for 5000 simulated realistic cases using the original Eqs. (4) to (6). In comparison, the lower panels of FIG. 7 show the residual sphere (left panel) and cylinder (right panel) for a 6 mm pupil after correction of the scaling factors for 5000 simulated realistic cases using the revised Eqs. (9) to (11).

From FIG. 7, it can be seen that after the scaling factor revision, the spread of the residual error in sphere and cylinder becomes tighter. Therefore, in a normal condition, it is not expected that any treatment would fail. However, if a treatment does not satisfy a validation test, it can be inferred that something unexpected may have happened. In such instances, the treatment table can be disqualified, and the treatment will not be applied to the patient. Hence, this example illustrates that for validating treatment tables, a set of numerical formulas can be developed and validated with multiple Monte Carlo simulations of 5000 cases for each optical zone of 4, 5, 6, and 7 mm.

Embodiments of the present invention encompass systems and methods for estimating or determining a scaling factor. Such techniques may involve constructing a theoretical Munnerlyn shape for all refractive cases covered by the VSS Refractive™ technique (e.g. S and C with increment of 0.25 D), calculating a decomposed refraction over a 4 mm diameter, and regressing using a multivariate quadratic regression model. Embodiments may also include calculating a wavefront refraction over a pupil dimension (e.g. assuming the wavefront diameter is not smaller than the pupil dimension), and converting the refraction to a vertex distance. Embodiments may also include calculating a 2D Munnerlyn shape, decomposing a surface into Zernike coefficients, calculating Zernike polynomials of each term, calculating Zernike polynomials of arbitrary size and returning a 2-D surface mesh.

Embodiments of the present invention further encompass systems and methods based on validation with a Monte Carlo Simulation. Exemplary techniques may involve performing a validation using Monte Carlo simulation which ensures that implementation of a validation technique passes all regular cases within a proposed range, for example a proposed −15 to +7 DS and −6 to +6 DC range for the VSS Refractive™ procedure. Such approaches can be based on a proposed tolerance that is the same as or similar to a an exam qualification, such as 0.625 D for SE and 0.5 D for cylinder. For example, for a 6 mm optical zone (OZ) and 12.5 mm vertex, it is possible to input sphere, cylinder, and axis data corresponding to a vertex plane, and sphere, cylinder, and axis data corresponding to a corneal plane. Similarly, it is possible to output sphere, cylinder, and axis data corresponding to a corneal plane. Embodiments also encompass determining scaling factors for sphere, cylinder, and axis, and calculating scaled sphere, cylinder, and axis values for corneal and vertex planes. Further, embodiments include determining differences between sphere, cylinder, and axis values at a corneal plane. A Monte Carlo simulation can be run with multiple (e.g. 1000) random refractions. Embodiments include calculating a predicted refraction versus a decomposed refraction from the treatment targets. Embodiments may also include calculating a refraction on the corneal plane. In some cases, embodiments encompass determining sphere and cylinder scaling factors. Embodiments may also include determining an empirical scaling factor for Munnerlyn power, where S and C represent the refraction on a corneal surface. Refractions can be converted to the corneal plane, and scaling factors can be calculated based on corneal refractions.

The methods and apparatuses of the present invention may be provided in one or more kits for such use. The kits may comprise a system for profiling an optical surface, such as an optical surface of an eye, and instructions for use. Optionally, such kits may further include any of the other system components described in relation to the present invention and any other materials or items relevant to the present invention. The instructions for use can set forth any of the methods as described herein.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

All patents, patent publications, patent applications, journal articles, books, technical references, and the like discussed in the instant disclosure are incorporated herein by reference in their entirety for all purposes.

While the above provides a full and complete disclosure of the preferred embodiments of the present invention, various modifications, alternate constructions and equivalents may be employed as desired. Therefore, the above description and illustrations should not be construed as limiting the invention, which can be defined by the appended claims.

What is claimed is:

1. A method of evaluating a treatment table for use in an ophthalmologic refractive surgery for a patient, the method comprising:
   inputting a treatment table containing laser ablation instructions for treating the patient into a treatment instructions module;
   determining a simulated ablation for the patient based on the laser ablation instructions with a simulation ablation module;
   determining an expected optical refraction for the patient based on the simulated ablation with an expected optical refraction module, wherein the expected optical refraction for the patient corresponds to high order aberration information comprising a third order aberration or a fourth order aberration;
   inputting an intended optical refraction for the patient into an intended refraction module, wherein the intended optical refraction for the patient corresponds to high order aberration information comprising a third order aberration or a fourth order aberration; and
   evaluating the treatment table by comparing the high order aberration information corresponding to the expected and intended optical refractions for the patient with a comparison module.

2. A method of evaluating a treatment table for use in an ophthalmologic refractive surgery for a patient, the method comprising:
   inputting a treatment table containing laser ablation instructions for treating the patient into a treatment instructions module;
   determining a simulated ablation for the patient based on the laser ablation instructions with a simulation ablation module;

inputting a pupil dimension of the patient into a pupil dimension module;

determining an expected optical refraction for the patient based on the pupil dimension and the simulated ablation with an expected optical refraction module, wherein the expected optical refraction for the patient is dependent on a sphere ophthalmic term characterized by a set of second radial order polynomial terms;

inputting an intended optical refraction for the patient into an intended refraction module, wherein the intended optical refraction for the patient is dependent on a sphere ophthalmic term; and evaluating the treatment table by comparing the expected and intended optical refractions for the patient with a comparison module.

3. The method according to claim 2, wherein the expected optical refraction and the intended optical refraction each correspond to a common plane.

4. The method according to claim 2, wherein the expected optical refraction and the intended optical refraction each correspond to a corneal plane.

5. The method according to claim 2, wherein the pupil dimension of the patient corresponds to a wavefront diameter related to a wavefront measurement of the patient.

6. The method according to claim 5, wherein the pupil dimensional of the patient comprises a pupil diameter that is equivalent to the wavefront diameter.

7. The method according to claim 2, wherein the pupil dimension of the patient comprises a pupil diameter of about 4 mm.

8. The method according to claim 2, further comprising determining if a difference between the expected and intended optical refractions for the patient is within a pre-defined tolerance.

9. The method according to claim 8, further comprising qualifying the treatment table for use in the ophthalmologic refractive surgery for the patient if the difference between the expected and intended optical refractions is within the pre-defined tolerance.

10. The method according to claim 8, further comprising disqualifying the treatment table for use in the ophthalmologic refractive surgery for the patient if the difference between the expected and intended optical refractions is not within the pre-defined tolerance.

11. A method of evaluating a treatment table for use in an ophthalmologic refractive surgery for a patient, the method comprising:

inputting a treatment table containing laser ablation instructions for treating the patient into a treatment instructions module;

determining a simulated ablation for the patient based on the laser ablation instructions with a simulation ablation module;

inputting a pupil dimension of the patient into a pupil dimension module;

determining an expected optical refraction for the patient based on the pupil dimension and the simulated ablation with an expected optical refraction module, wherein the expected optical refraction for the patient is dependent on a spherical equivalent ophthalmic term, a cylinder ophthalmic term, and a cylinder angle ophthalmic term;

inputting an intended optical refraction for the patient into an intended refraction module, wherein the intended optical refraction for the patient is dependent on a spherical equivalent ophthalmic term, a cylinder ophthalmic term, and a cylinder angle ophthalmic term; and evaluating the treatment table by comparing the expected and intended optical refractions for the patient with a comparison module.

12. The method according to claim 11, wherein the evaluating step comprises comparing the spherical equivalent ophthalmic term corresponding to the expected optical refraction with the spherical equivalent ophthalmic term corresponding to the intended optical refraction.

13. The method according to claim 11, wherein the evaluating step comprises comparing the cylinder ophthalmic term corresponding to the expected optical refraction with the cylinder ophthalmic term corresponding to the intended optical refraction.

14. The method according to claim 11, wherein the evaluating step comprises comparing the cylinder angle ophthalmic term corresponding to the expected optical refraction with the cylinder angle ophthalmic term corresponding to the intended optical refraction.

15. The method according to claim 11, wherein the evaluating step comprises comparing the spherical equivalent ophthalmic term corresponding to the expected optical refraction with the spherical equivalent ophthalmic term corresponding to the intended optical refraction, comparing the cylinder ophthalmic term corresponding to the expected optical refraction with the cylinder ophthalmic term corresponding to the intended optical refraction, and comparing the cylinder angle ophthalmic term corresponding to the expected optical refraction with the cylinder angle ophthalmic term corresponding to the intended optical refraction.

16. The method according to claim 11, wherein the expected optical refraction and the intended optical refraction each correspond to a common plane.

17. The method according to claim 11, wherein the expected optical refraction and the intended optical refraction each correspond to a corneal plane.

18. The method according to claim 11, wherein the pupil dimension of the patient corresponds to a wavefront diameter related to a wavefront measurement of the patient.

19. The method according to claim 18, wherein the pupil dimensional of the patient comprises a pupil diameter that is equivalent to the wavefront diameter.

20. The method according to claim 11, further comprising determining if a difference between the expected and intended optical refractions for the patient is within a pre-defined tolerance.

* * * * *